(12) United States Patent
Khamehchi et al.

(10) Patent No.: US 11,398,330 B2
(45) Date of Patent: Jul. 26, 2022

(54) THERAPEUTIC FIELD DIRECTIONAL MAGNETIC ARRAY

(71) Applicant: Magmedics, LLC, East Lansing, MI (US)

(72) Inventors: Mohammad Amin Khamehchi, San Diego, CA (US); Kasey R. Lund, East Lansing, MI (US)

(73) Assignee: Magmedics, LLC, East Lansing, MI (US)

( * ) Notice: Subject to any disclaimer, the term of this patent is extended or adjusted under 35 U.S.C. 154(b) by 361 days.

(21) Appl. No.: 16/543,059

(22) Filed: Aug. 16, 2019

(65) Prior Publication Data

US 2020/0121940 A1 Apr. 23, 2020

Related U.S. Application Data

(60) Provisional application No. 62/748,174, filed on Oct. 19, 2018.

(51) Int. Cl.
*H01F 7/02* (2006.01)
*A61N 2/00* (2006.01)
*A61N 2/06* (2006.01)

(52) U.S. Cl.
CPC ............. *H01F 7/021* (2013.01); *A61N 2/004* (2013.01); *A61N 2/06* (2013.01); *H01F 7/0221* (2013.01)

(58) Field of Classification Search
CPC ...... H01F 7/021; H01F 7/0221; H01F 7/0294; A61N 2/004; A61N 2/06
See application file for complete search history.

(56) References Cited

U.S. PATENT DOCUMENTS

| | | | | |
|---|---|---|---|---|
| 3,168,686 | A * | 2/1965 | Nicholas | H01F 7/02 335/306 |
| 4,392,078 | A * | 7/1983 | Noble | G03B 7/09976 315/3 |
| 4,837,542 | A * | 6/1989 | Leopold | G01R 33/383 315/5.35 |
| 5,049,053 | A * | 9/1991 | Tabaru | H01F 7/021 425/3 |
| 5,216,401 | A * | 6/1993 | Leopold | G01R 33/383 335/306 |
| 5,382,936 | A * | 1/1995 | Leopold | G01R 33/383 335/306 |
| 5,396,209 | A * | 3/1995 | Leopold | H01F 7/0278 324/318 |

(Continued)

FOREIGN PATENT DOCUMENTS

WO WO 2018/085330 5/2018

OTHER PUBLICATIONS

R. Tao and K. Huang, Reducing blood viscosity with magnetic fields, Physical Review E 00.001900 May 2011.

(Continued)

*Primary Examiner* — Mohamad A Musleh
(74) *Attorney, Agent, or Firm* — Gunther Evanina; Butzel Long

(57) ABSTRACT

An array of permanent magnets and magnetic materials create a large focused magnetic field capable of reducing the viscosity of blood in a human subject, and consequently reducing the blood pressure of the subject. The magnets can be arranged in highly tunable and customizable configurations suited to unique and individual applications.

16 Claims, 4 Drawing Sheets

(56) References Cited

U.S. PATENT DOCUMENTS

| | | | | |
|---|---|---|---|---|
| 5,491,459 | A * | 2/1996 | Leopold | H01F 7/0278 315/5.35 |
| 5,990,774 | A * | 11/1999 | Leopold | H01F 13/003 335/306 |
| 6,680,663 | B1 * | 1/2004 | Lee | G01R 33/383 335/302 |
| 7,199,689 | B1 * | 4/2007 | Abele | G01R 33/383 324/319 |
| 7,900,343 | B1 * | 3/2011 | Leopold | H01F 7/021 29/607 |
| 8,405,479 | B1 * | 3/2013 | Cleveland | H01F 7/0273 335/306 |
| 9,159,479 | B2 * | 10/2015 | Rotem | H01F 7/02 |
| 2002/0113678 | A1 * | 8/2002 | Creighton | H01F 7/0273 335/306 |
| 2010/0280303 | A1 | 11/2010 | Dietz | |
| 2017/0093215 | A1 * | 3/2017 | Ng | H02J 50/10 |

OTHER PUBLICATIONS

Q.L. Peng et al., Axial magnetic field produced by axially and radially magnetized permanent rings, Journal of Magnetism and Magnetic Materials 268 (2004) pp. 165-169.

Giorgio Moresi et al., Miniature permanent magnet for table-top NMR, Concepts in Magnetic Resonance Part B (Magnetic Resonance Engineering, vol. 19B(1) (2003) pp. 35-43.

Farhad Ali et al., Flow of magnetic particles in blood with isothermal heating: A fractional model for two-phase flow, Journal of Magnetism and Magnetic Materials, 456 (2018) pp. 413-422.

Ashkan-Javadzadegan et al., Effect of magnetic field on haemodynamic perturbations in atherosclerotic coronary arteries, Journal of Medical Engineering & Technology, vol. 42, No. 2 (2018) pp. 148-156.

Anna Marcinkowska-Gapinska and Honorata Nawrocka-Bogusz, Analysis of the magnetic field influence on the rheological properties of healthy persons blood, BioMed Research International, vol. 2013, pp. 1-7.

Herbert A. Leupold et al., Multi-Tesla permanent magnet field sources, J. Appl. Phys. 73 (10) (1993), pp. 6861-6863.

Gary Null, Biomagnetic Healing,(80 pages).

Herbert A. Leopold and Ernest Potenziani II, An overview of modern permanent magnet design, Electronics Technology and Devices Laboratory, US Army Laboratory Command, Aug. 1990 (71 pages).

Chiyoji Ohkubo and Hideyuki Okano, Magnetic field influences on the microcirculation, ResearchGate, Chapter—Mar. 2015, pp. 103-128.

* cited by examiner

THERAPEUTIC FIELD DIRECTIONAL MAGNETIC ARRAY

CROSS-REFERENCE TO RELATED APPLICATIONS

This application claims priority to Provisional Application No. 62/748,174, filed Oct. 19, 2018, which is incorporated herein by reference in its entirety.

FIELD OF THE DISCLOSURE

This disclosure relates to magnetic devices and more particularly to an array of permanent magnets that effectively focus and confine a magnetic field within a cavity.

BACKGROUND OF THE DISCLOSURE

Hypertension (blood pressure) is an increasingly concerning health problem in both the developing and developed countries. If hypertension is ignored, it can lead to more serious health problems such as stroke or artery damage. Prescription drugs are currently the solution to hypertension. However, prescription drugs have their disadvantages. These include lethal effects when mixed with other medications and adverse effects on the stomach to name a few.

Electromagnetic therapeutic bracelets and rings that claim they can reduce the blood pressure are not a new concept. However, all available bracelets and rings on the market do not have any measurable effect on human health. They have very weak magnetic field strengths around them which result in insignificant magnetic interactions with the blood cells. In more technical terms, the energy of these interactions is below the thermal noise in the human body. The therapeutic characteristics of these devices are not backed by any measurable concrete science. All of the available therapeutic magnetic bracelets and rings on the market are based on anecdotal stories and individual experiences. These devices are said to have relaxing and mood enhancing effects. While these individual stories and claims may be true, none of the available devices provide a magnetic field that is strong enough to have measurable effects on human subjects. Additionally, all of the available magnetic therapy bracelets and rings are designed with form or aesthetic quality over functionality. Furthermore, the field orientation of these devices are either perpendicular to the flow of blood in the veins and arteries, or they have a non-uniform alternating magnetic field.

SUMMARY OF THE DISCLOSURE

The present invention seeks to provide a solution to the hypertension problem by providing a permanent magnet array that can be used to magnetize the red blood cells and reduce the viscosity of the blood fluid, ultimately reducing the user's blood pressure. Prior to this invention, large electromagnets were used to reproducibly lower blood viscosity. However, they used very large and expensive magnets to achieve these results. Because of the size and cost of these type of magnets, as well as high energy use and cooling requirements, it is not reasonable for a consumer or health care provider to purchase magnets of this size.

DETAILED DESCRIPTION

The therapeutic field directional permanent magnet array disclosed herein is a novel configuration of permanent magnets and magnetic materials such as, but not limited to, soft iron, and mu-metal materials to generate a large directional magnetic field. The array of permanent magnets generates a large static magnetic field parallel or anti-parallel to the blood flow. The arrangement of the magnets and the magnetic materials focuses the field around the user's blood vessels and veins, and reduce the field that exists outside of the apparatus. The strength of the magnetic field can vary. For therapeutic applications, the field strength can be above the thermal threshold, such as from approximately 1 Tesla to approximately 1.3 Tesla. The device creates a field that is parallel to the veins and arteries thus being parallel to blood flow. The large magnetic field will polarize the hemoglobin within the red blood cells in the targeted veins and arteries in order to lower the viscosity of the user's blood and reduce their blood pressure. This design is scalable to be small enough to wear on a finger like a ring, or large enough to place one's arm or leg inside the high field region.

Figure 1:
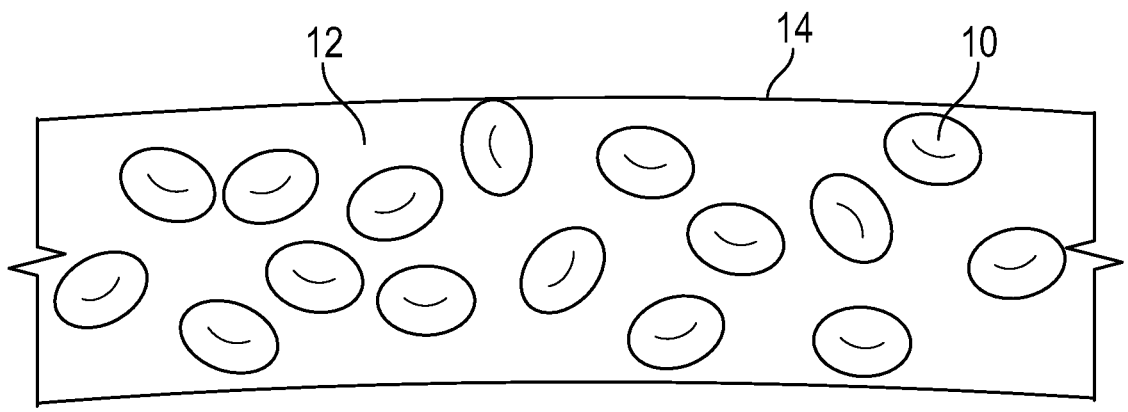
FIG. 1 represents a blood vessel or vein with red blood cells suspended in plasma.

An array of permanent magnets are oriented such that their combined field strength can be about 1 Tesla in areas such as the wrist, ankle or digit. The strong magnetic field will polarize the red blood cells 10 (erythrocytes) suspended in plasma 12 in the veins and arteries 14 (see FIGS. 1 and 2). The polarized blood cells then form chains in the veins and arteries. It has been established (Tao et al. "Reducing Blood Viscosity with Magnetic Fields", Physical Review E 00, pages 001900-1-001900-5, (2011)) that chains of blood cells will have a lower viscosity than that of randomly distributed blood cells.

Figure 2:
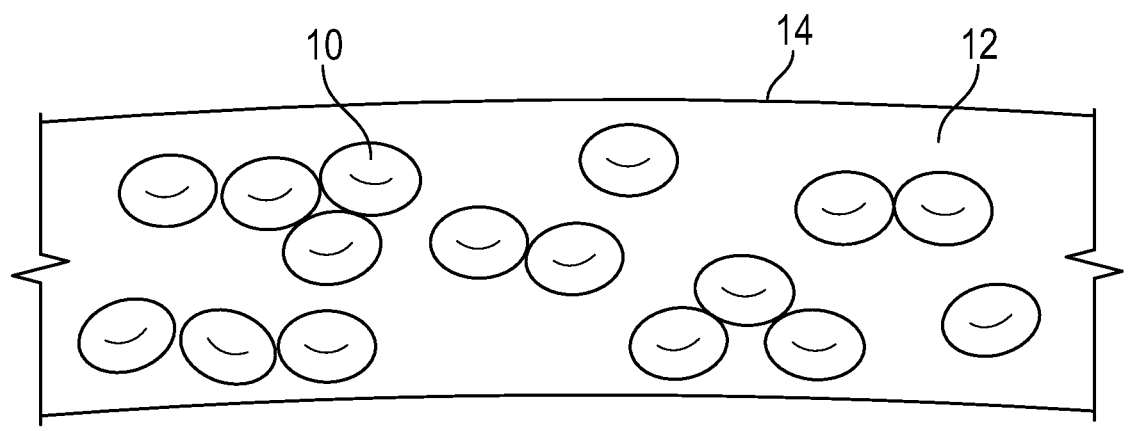
FIG. 2 represents a vessel or vein similar to FIG. 1, when a static magnetic field is applied in the direction of the vessel or vein.
Figure 3:
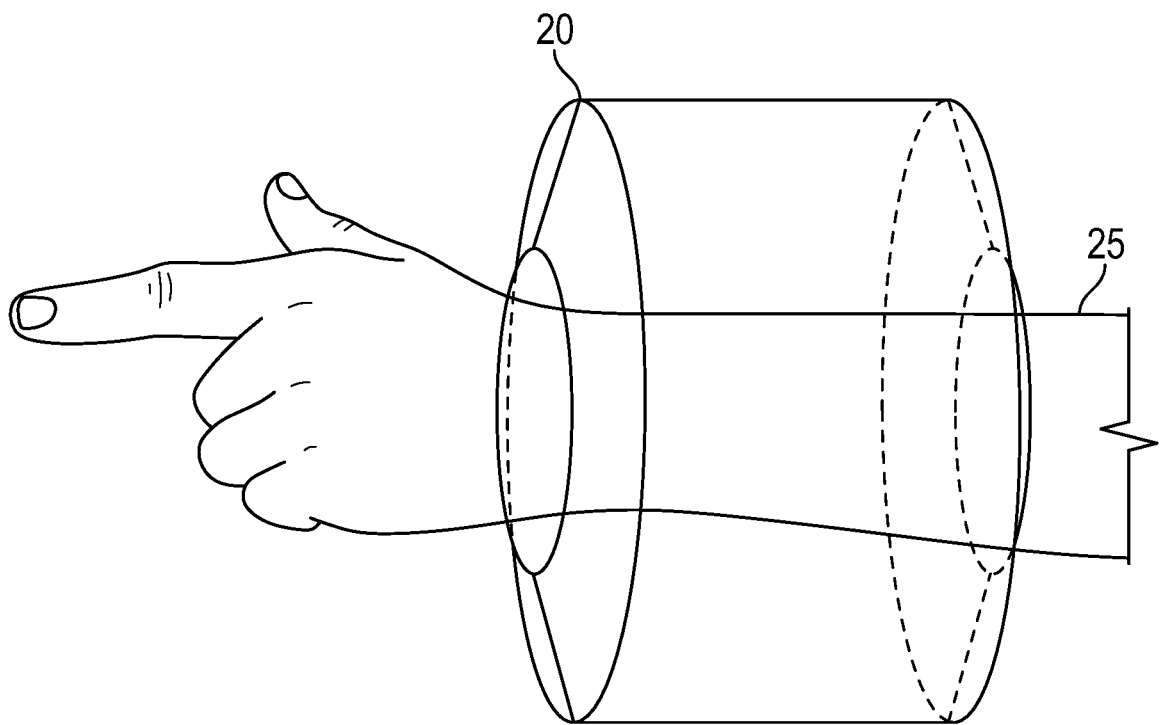
FIG. 3 is a perspective view of a magnetic device in accordance with this disclosure configured to therapeutically apply a magnetic field to the wrist and/or lower arm of a human subject in need of treatment.
Figure 4:
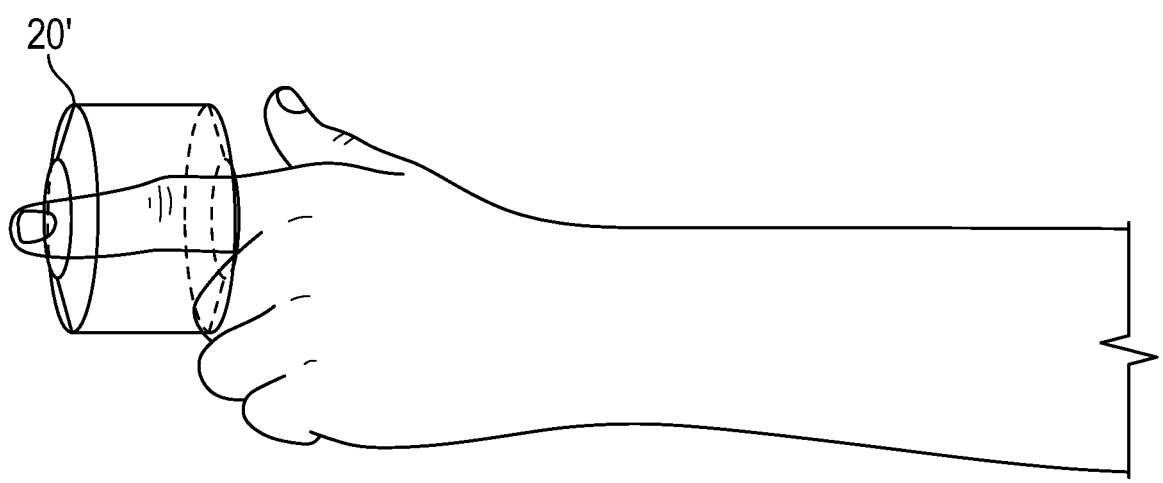
FIG. 4 is a perspective view of a magnetic device in accordance with this disclosure configured to therapeutically apply a magnetic field to the finger of a human subject in need of treatment.

The devices illustrated in FIGS. 3-6 can be used to reduce blood pressure in a mammal, such as a human user. First, the user places the device on their arm, leg, or finger. For example, FIGS. 3 and 4 show the device 20 on the user's arm 25 and finger 30, respectively. The user will then secure the bracelet/ring in place and remain still while they are using the device, sitting or standing. The device is left in place for a prescribed treatment time (usually 1-20 mins) depending on the field strength and particular application. During the treatment time, the red blood cells will begin to self-organize and form small chains similar to what is illustrated in FIG. 2. The direction and orientation of the chains will be perpendicular to the symmetry axis of the red blood cells. In this way, the polarization and aggregation will not affect the red cells ability to deliver oxygen to the body and remove carbon dioxide. The organized chains of red blood cells will lower the viscosity of the blood and reduce the user's blood pressure.

Once the treatment time is complete, the user will remove the device or remove the limb from the device. The beneficial effects caused by wearing the device will depend on the length of the treatment time and the half-life of the red blood cell aggregations in the bloodstream. The user will be free to go about their daily tasks and duties and periodically re-apply the device again throughout the day, each time lowering their blood viscosity and blood pressure. The device can be hinged and provided with a latch or other mechanism to facilitate securement of the device around a limb and removed therefrom.

Another way of using the device would be implantation. In this case, a small magnetic assembly is implanted inside the patient's body such that the array applies an axial magnetic field to the bloodstream. This way, the patient will be free of periodic usage of the device (i.e., the device can always provide a therapeutic effect). Such implantable arrays can be coated with materials that are not rejected by the body, such as but not limited to silicone, polyethylene, titanium, polyurethane foam, etc. The implantable magnetic array is configured to enclose a blood vessel or vein, such as with a clamshell structure in which the structure is divided into two or more sections and opens and recloses to allow routing of the blood vessel/vein through a longitudinal bore, or the blood vessel/vein can be severed and then stitched to opposite ends of the magnetic array. The second method does not require a clamshell mechanism and might be more cost effective.

Figure 5:
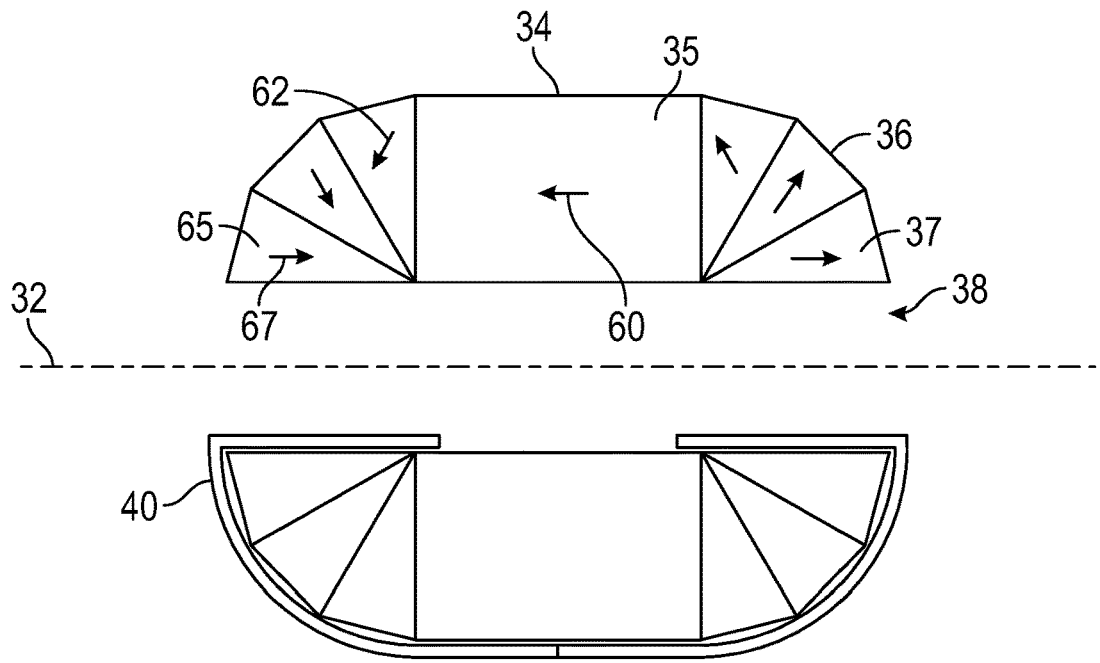
FIG. 5 is a transverse cross-sectional view of the device shown in FIG. 4.
Figure 6:
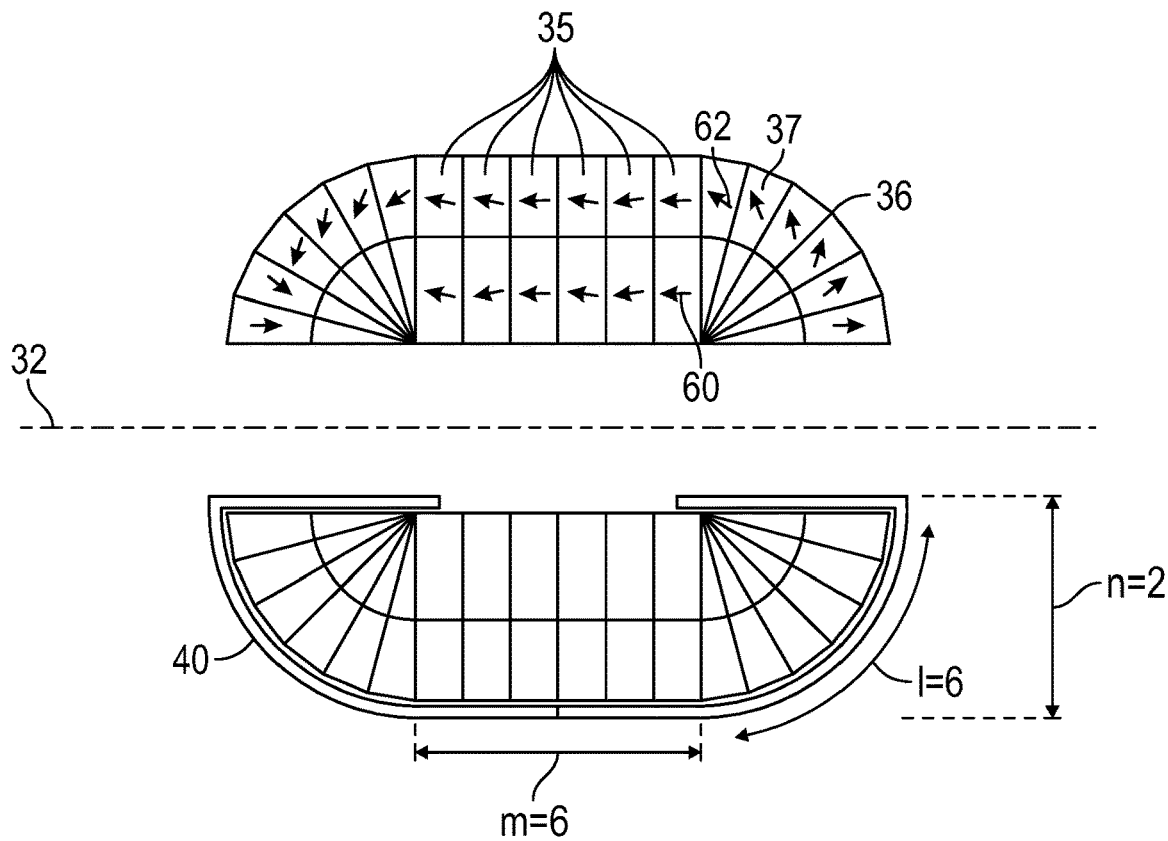
FIG. 6 is a transverse cross-sectional view of an alternative embodiment of the magnetic devices disclosed herein.

Referring to FIGS. 5 and 6, the symmetry axis of the device is indicated by 32. The device can have symmetries including, but not limited to, cylindrical, elliptical, or conical around the symmetry axis 32. Variations from symmetry are also possible to optimize its effectiveness for each application and patient. As shown in FIG. 6, the center section or magnet array 34 has m magnet layers along the axial direction of the device, n magnet layers in the radial direction, l magnets arranged in the polar angle direction, and k magnets (not illustrated) arranged around the symmetry axis 32. FIG. 5 shows an array with m=1, n=1, l=3, and k is not shown. FIG. 6 shows an array with m=6, n=2, l=6, and k is not shown.

The inner and outer radii of each section can vary depending on the desired magnetic profile that is required for a particular application, such as a patient's conditions and dimensions of their body part. Varying the radii changes the magnetic field profile which can make the device more efficient for a wider variety of applications. The magnetization direction of each magnet in this array can be slightly varied in a way that it maximizes the effectiveness of the device for the specific case of use or location to be applied. The magnetization of the magnet or magnets corresponding with center section 34 are approximately aligned with the passageway axis 32 (more nearly parallel with axis 32 than are the diameter of magnitude of the magnets in the end caps 36).

The end-caps 36 exists on both sides of the device. It is possible to modify or remove one or more parts of the end-caps from one side of the device and still generate large amounts of magnetic field. However, a symmetric design in the axial direction can generate larger magnetic fields. The end-caps 36 comprise an arrangement of permanent magnets that focus the magnetic field in the axial direction (e.g., along the symmetry axis 32). It is not necessary to keep the dimensions of the radial sections the same and the number of layers and sections can be optimized for the application. The number of sectors can be as low as 1 in the polar angular direction. However, more sections allow for a more customized magnetic field and generally larger magnitudes of the magnetic field. Magnetic shielding 40 can extend along the outside of the device to reduce the magnetic field on the outside for safety reasons. Shielding can also extend along the inside of the device to further shape the magnetic field for higher efficiency. Suitable shielding materials include generally any nickel, iron or cobalt based ferromagnetic material or mu-metal (i.e., nickel-Tron ferromagnetic alloy).

The device can have a clam shell configuration with hinges on one side and a closure on an opposite side, or could be comprised of three or more segments that can be hinged and/or otherwise fastened together (e.g., glued or cemented together).

In its simplest form and with symmetric magnet arrangement, this device will generate a magnetic field that is cyclic symmetric in its active area.

Assuming that we have a total of m×n×k+2×n×l×k magnets in which, in is the number of magnet layers in the axial direction, n is the number of layers in the radial direction, k is the number of magnets around the symmetry axis 32, l is the number of sectors in the polar angle direction, the number of degrees of freedom due to magnetization only will be $$2kn(m+2l),$$

because each magnet will have two degrees of freedom for its magnetization direction. We also have more degrees of freedom due to the dimensions and shape of the magnets. These degrees of freedom allow us to maximize the effectiveness of the device on patients. For example, for a magnetic array with m=5, n=2, k=8, and l=3, the number of degrees of freedom will be 352. Therefore, we can used these degrees of freedom to maximize the field in the direction of a targeted artery or vein along any path, which can be achieved by maximizing the line integral of the magnetic field (w) along the path of the vein/vessel, $$w = \oint_a^b B \cdot dl.$$

Figure 7:
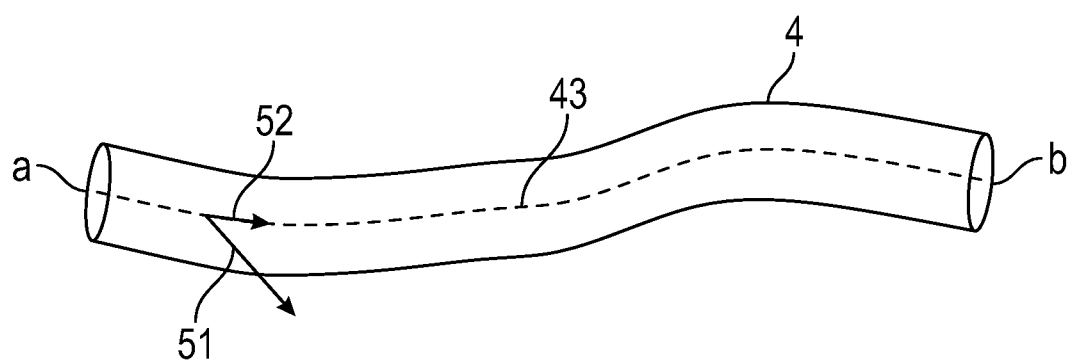
FIG. 7 is a schematic illustration of a longer segment of a vein or artery.

Here B is the magnetic field vector and dl is the differential path vector along the vessel/vein path. FIG. 7 schematically shows a vein/vessel 14 which is extended along path 43. dl and B are represented by 52 and 51 in the figure respectively. In other words, the flexibility of this design allows one to customize the direction of the magnetic field to any patient.

The permanent magnets comprising the array can be comprised of a rare-earth ferromagnetic element. Suitable materials include neodymium (Nd Fe B), samarium cobalt (Sm Co), ferrite, alnico, or other suitable magnetic material, with neodymium being generally preferred. The magnets can be held together in the arranged arrangement using any suitable bonding material, such as an epoxy resin adhesive (e.g., Araldite Rapid or Locktite Industrial strength adhesive). Other joining techniques, such as brazing or soldering, may be employed.

The devices disclosed herein confine and focus the magnetic field within a cavity or passageway 38.

The devices can be miniaturized for implantation over blood vessels, such devices can be provided with a ceramic or titanium coating to improve biocompatibility.

Figure 8:
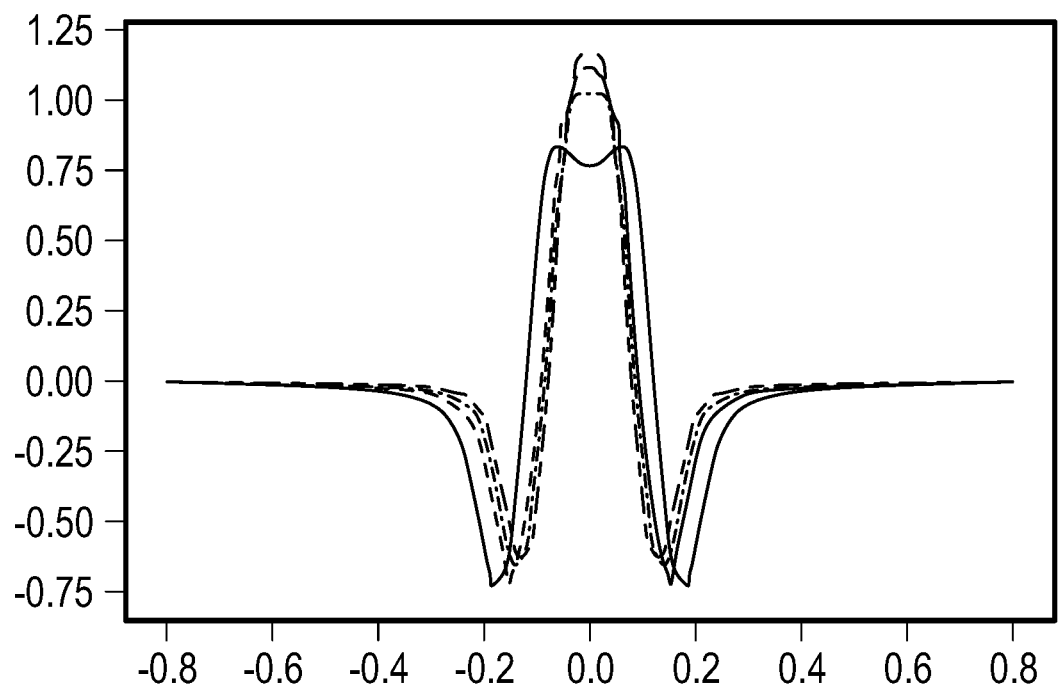
FIG. 8 is a graph showing magnetic field strength as a function of distance from the centerline of a passageway.

FIG. 8 shows the magnetic field in the axial direction on the axis of the device. The Y axis is in Tesla, and the X axis is in Meters, measured from the centerline 32 of passageway 38 (FIG. 5), showing some typical field strengths seen for various dimensions. The magnetic field becomes negative in the wings, but it stays positive at the center. The integral of the magnetic field along the axial direction will have net position value, which can help lower blood viscosity.

In certain embodiments, the magnetic device includes a plurality of permanent magnets 35, 37 arranged into a structure having a passageway 38 aligned with a longitudinal axis 32 of the structure, the structure including a center section 34 having one or more permanent magnets 35 and having a magnetization 60 aligned with the passageway, the structure further including an end section 36 at each of two opposite ends of the center section, each end section having a cross-sectional profile transverse to the length direction that tapers from the ends of the center section, each end section comprising a plurality of permanent magnets 37, each permanent magnet having a magnetization 62 that is at an angle relative to the magnetization of the center section.

In certain embodiments, each end section or cap 36 comprises a plurality of permanent magnets, including at least one layer of permanent magnets arranged around the longitudinal axis 32 and disposed adjacent an end of the center section, and at least one layer of permanent magnets arranged around the longitudinal axis and disposed adjacent the passageway. The magnetizations of the permanent magnets adjacent the end of the center section are oriented in a direction between the direction of the magnetization of the center section and a direction extending perpendicularly from a centerline of the passageway, and the magnetization 67 of the permanent magnets 65 adjacent the passageway aligned in a direction of the magnetization of the center section.

In certain embodiments, the device includes a plurality of layers of permanent magnets disposed between the layer of permanent magnets disposed adjacent the end of the center section and the layer of permanent magnets disposed adjacent the passageway. The angle of the magnetization of the magnets comprising the end-caps 36 vary from one magnet to the adjacent magnet. In the illustrated embodiments (FIGS. 5 and 6), the direction of magnetization of each magnet of caps 36 differs from that of adjacent magnets.

In certain embodiments, the center section can comprise a single permanent magnet, or a plurality of permanent magnets. The center section can have a uniform cross-sectional profile transverse to the length direction, a polygonal cross-sectional profile transverse to the length direction, or other configuration. Each section can have a circular cross-sectional profile transverse to the length direction. Each section can be comprised of a plurality of radially adjacent layers. The center section can have a cylindrical shape and each of the end sections can have a frustoconical shape, or the center section can have a cylindrical shape and each of the end sections can have a hemispherical shape. The passageway can have a size or diameter varying from less than 1 mm (e.g., 100 µm) to several centimeters (e.g., 20 cm).

The devices disclosed herein are fully scalable provided that all dimensions are scaled equally.

The above description is intended to be illustrative and not restrictive. Many embodiments and applications other than the examples provided would be apparent upon reading the above description. The scope of the invention should be determined with reference to the appended claims along with the full scope of equivalents to which such claims are entitled. It is anticipated and intended that future developments will occur, and that the disclosed systems and methods will be incorporated into such future embodiments.

All terms used in the claims are intended to be given their broadest reasonable constructions and their ordinary meanings as understood by those knowledgeable in the technologies described herein unless an explicit indication to the contrary is made herein. In particular, use of the singular articles such as "a," "the," "said," etc., should be read to recite one or more of the indicated elements unless a claim recites an explicit limitation to the contrary.

What is claimed is:

1. A magnetic device, comprising:
   a plurality of permanent magnets arranged into a structure having a passageway aligned with a longitudinal axis of the structure, the structure including a center section having one or more permanent magnets at least one of which has magnetization approximately aligned with the passageway, the structure further including an end section at each of two opposite ends of the center section, each end section having a cross-sectional profile transverse to the length direction that tapers from the ends of the center section, each end section comprising a plurality of permanent magnets having a magnetization that is at an angle relative to the magnetization of the center section,
   wherein each end section comprises a plurality of permanent magnets, including at least one layer of permanent magnets arranged around the longitudinal axis and disposed adjacent an end of the center section, at least one layer of permanent magnets arranged around the longitudinal axis and disposed adjacent the passageway, the magnetization of the permanent magnets adjacent the end of the center section being oriented in a direction between the direction of the magnetization of the center section and a direction extending perpendicularly from a centerline of the passageway, and the magnetization of the permanent magnets adjacent the passageway aligned in a direction opposite the direction of the magnetization of the center section.

2. The device of claim 1, wherein each of the plurality of permanent magnets of the end sections has a direction of magnetization that is at an angle relative to the direction of magnetization of an adjacent permanent magnet.

3. The device of claim 1, wherein the center section comprises a single permanent magnet.

4. The device of claim 1, wherein the center section comprises a plurality of permanent magnets.

5. The device of claim 1, wherein the center section has a uniform cross-sectional profile transverse to the length direction.

6. The device of claim 1, wherein each section has a polygonal cross-sectional profile transverse to the length direction.

7. The device of claim 1, wherein each section has circular cross-sectional profile transverse to the length direction.

8. The device of claim 1, wherein each section is comprised of a plurality of radially adjacent layers.

9. The device of claim 1, wherein the center section has a cylindrical shape and each of the end sections has a frustoconical shape.

10. The device of claim 1, wherein the center section has a cylindrical shape and each of the end sections has a hemispherical shape.

11. The device of claim 1, wherein the magnetic field strength in the passageway is greater than or about 1 Tesla.

12. The device of claim 1, wherein the passageway has a diameter of from about 100 µm to 20 cm.

13. The device of claim 12, in which the permanent magnets are comprised of a rare earth ferromagnetic material.

14. The device of claim 12, in which the permanent magnets are comprised of neodymium.

15. The device of claim 12, in which the magnetic field strength in the passageway is greater than or about 1 Tesla.

16. The device of claim 12, further comprising a layer of magnetic shielding surrounding outer surfaces of the device.

* * * * *